United States Patent
Heuscher et al.

(10) Patent No.: US 6,775,346 B2
(45) Date of Patent: Aug. 10, 2004

(54) CONEBEAM COMPUTED TOMOGRAPHY IMAGING

(75) Inventors: Dominic J. Heuscher, Aurora, OH (US); Kevin M. Brown, Mentor-on-the-Lake, OH (US); Patrick J. Kling, Mentor, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 102 days.

(21) Appl. No.: 10/274,816

(22) Filed: Oct. 21, 2002

(65) Prior Publication Data

US 2004/0076265 A1 Apr. 22, 2004

(51) Int. Cl.[7] ................................................ A61B 6/03
(52) U.S. Cl. ............................. 378/4; 378/15; 378/901
(58) Field of Search ............................. 378/4, 8, 15, 19, 378/901

(56) References Cited

U.S. PATENT DOCUMENTS

| | | | |
|---|---|---|---|
| 4,583,241 A | 4/1986 | Walters | 378/19 |
| 5,008,822 A | 4/1991 | Brunnett et al. | 364/413.21 |
| 5,262,946 A | 11/1993 | Heuscher | 364/413.18 |
| 5,430,783 A | 7/1995 | Hu et al. | 378/15 |
| 5,485,493 A | 1/1996 | Heuscher et al. | 378/686 |
| 5,999,587 A * | 12/1999 | Ning et al. | 378/4 |
| 6,269,141 B1 | 7/2001 | Proksa et al. | 378/19 |
| 6,324,242 B1 | 11/2001 | Pan | 378/4 |
| 6,408,042 B1 | 6/2002 | Hsieh | 378/4 |

* cited by examiner

Primary Examiner—David V Bruce
(74) Attorney, Agent, or Firm—John J. Fry

(57) ABSTRACT

An image reconstruction method for reconstructing cone or wedge-beam computed tomography projection data includes re-binning (50) the projection data to associate projection data having the similar angular orientation (θ), weighting (60) projection data based on at least one of its angular orientation (θ) and its location within a detector aperture (20), and reconstructing (66) the weighted projection data (64) to form a volume image representation (70). In one preferred embodiment, the weighting (60) includes distributing (56) re-binned projection data (52) associated with a selected image element which one of (a) has the same angular orientation (θ) and (b) is angularly separated by integer multiples of 180° into a selected one or more of a plurality of parallel processing pipelines ($60_m$), and combining (62) the outputs of the selected one or more parallel processing pipelines ($60_m$) to produce weighted projection data (64).

32 Claims, 12 Drawing Sheets

CONEBEAM COMPUTED TOMOGRAPHY IMAGING

BACKGROUND OF THE INVENTION

The present invention relates to the computed tomography and medical imaging arts. It particularly relates to computed tomography (CT) imaging using an x-ray source that produces a conical beam (conebeam CT) and which traverses a helical orbit relative to an imaging subject, and will be described with particular reference thereto. However, the invention will also find application in conjunction with other types of CT imaging including multi-slice imaging, fan-beam CT, and the like, as well as in conjunction with other imaging techniques.

Computed tomography (CT) imaging has application in many areas involving non-invasive examination of internal features of a subject. For example, CT is applicable in security baggage examination and in clinical and diagnostic medical imaging. Regarding medical applications, CT has been employed for cardiac imaging, functional imaging of dynamically moving organs such as the lungs, blood perfusion imaging, and for other types of medical imaging. CT advantageously provides three-dimensional clinical imaging without injected radiopharmaeceuticals. However, CT sometimes suffers from limited acquisition speed. As an example, in a modern CT the x-ray source typically orbits the subject at about 120 rpm, corresponding to 0.25 seconds for data acquisition over 180°. Since a complete cardiac cycle period is about one second or less, the CT acquisition time can lead to motion blurring in cardiac imaging.

In CT imaging, an x-ray source transmits x-rays into an examination region where the x-rays are partially absorbed by a subject being imaged. Detectors arranged across the examination region from the x-ray source detect the x-rays after passing through the examination region. The detected x-ray intensity is characteristic of the absorption experienced as the x-rays pass through the examination region, and the output data is typically arranged in a projection data format. Using appropriate mathematical techniques, the projection data is reconstructed into an image representation characteristic of the subject or a portion thereof.

In early CT imaging, the x-ray source was narrowly collimated into a beam or thin wedge-shaped slice. The x-ray source was rotated about the examination region in a circular orbit, and the resulting projection data was reconstructed into a slice image. The subject was repetitively stepped through the examination region in a direction perpendicular to the slice plane to acquire a plurality of such image slices. Taken together, a stack of slices provides a three-dimensional characterization of the subject. Although this CT configuration simplified many mathematical aspects of the image reconstruction, it was slow. Furthermore, the collimation of the x-ray source greatly reduced the x-ray power, resulting in lowered signal-to-noise ratios.

Recently, CT imaging systems have been developed in which a conebeam x-ray source moves along a helical path obtained by simultaneously orbiting the x-ray source while advancing the subject. The conebeam x-ray source is coupled with a two-dimensional array of x-ray detectors which record conebeam transmission across the area of the conebeam. Helical conebeam CT continuously acquires divergent two dimensional projection data which greatly improves scanning speed, and the less aggressive collimation makes more efficient use of the x-ray source output.

However, the reconstructed helical conebeam CT image quality has in the past been degraded by image artifacts and other degradation modalities resulting from the poorly defined x-ray path geometry. Past reconstruction methods have also typically included image-degrading approximations which however were incorporated to allow the reconstruction speed to keep pace with the rapid data acquisition of the helical conebeam geometry.

For example, while a thin wedge-shaped x-ray beam (typically spanning four slices) can be treated as parallel x-ray paths, this approximation with wider conebeam CT data is complicated by the three-dimensional extent of the conical x-ray beam. With a helical source path, there is no single plane containing all the projection data intersecting a selected voxel or image plane in the examination region. Rather, the conebeam rays pass through each voxel at a myriad of different angles and directions, and occur when the x-ray source is at different angular and longitudinal positions. For exact reconstruction a computationally intense three-dimensional reconstruction is required. Such a reconstruction processor is disadvantageously slow due to the large number of computations involved. Moreover, numerous revolutions are needed to acquire the full set of rays through a given voxel. Hence, many past conebeam reconstruction processors have neglected to account for many three-dimensional effects, thus providing faster image reconstruction at the cost of degraded image quality, particularly for large cone angles.

The present invention contemplates an improved CT imaging apparatus and method which overcomes the aforementioned limitations and others.

SUMMARY OF THE INVENTION

According to one aspect of the invention, an image reconstruction method is disclosed for reconstructing cone or wedge-beam computed tomography projection data. Projection data is weighted based on at least one of its angular orientation and its location within a detector aperture. The weighted projection data is reconstructed to form a volume image representation.

According to another aspect of the invention, a computed tomography imaging apparatus for reconstructing cone or wedge beam projection data is disclosed. A weighting means is provided for weighting cone or wedge projection data based on at least one of its angular orientation and its location in a detector aperture. A reconstructing means is provided for reconstructing the weighted projection data to form a volume image representation.

One advantage of the present invention is that it improves temporal and spatial resolution of axial, spiral, as well as continuous conebeam CT images. One particular advantage of these improvements is reduced motion artifacts.

Another advantage of the present invention resides in selective application of detector aperture and angular weighting functions in reconstructing spiral conebeam data for applications such as cardiac imaging.

Another advantage of the present invention resides in efficient and flexible combination of complementary or redundant conebeam projection data from one or more half-cycles apart (i.e., combination of data that is congruent modulo 180°). Data combination is advantageously applicable in axial, spiral, and conebeam imaging. The combining is flexible to permit maximum use of the available reconstruction pipelines separately or in weighted combination.

Another advantage of the present invention resides in efficient mapping of projection data in the axial or Z-dimension onto the backprojection matrix using a non-linear recursive model particularly appropriate for conebeam geometries. The mapping process optionally incorporates planar, volume or other image sub-matrices.

Yet another advantage of the present invention resides in accommodation of data of varying CT acquisition geometries such as full-pitch conebeam, half-pitch conebeam, cardiac spiral conebeam, and continuous conebeam CT by selecting appropriate angular and aperture weighting values. The present invention is compatible with a wide range of conebeam reconstruction geometries, including n-PT geometries, wedge geometries, and the like.

Still yet another advantage of the present invention is compatibility with gated or dose modulated CT imaging.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
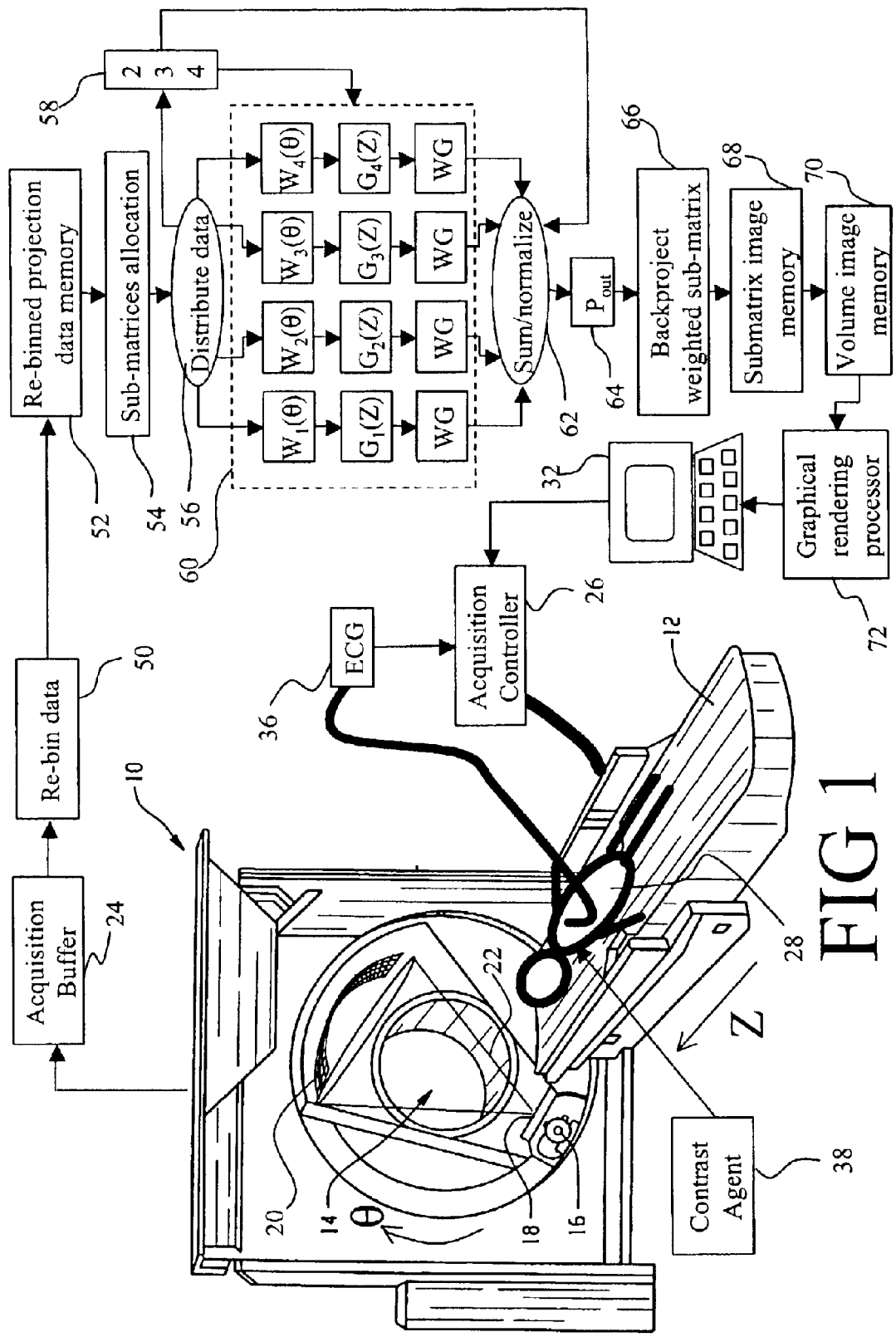
FIG. 1 shows a diagram of a computed tomography imaging system that suitably practices an embodiment of the invention.

With reference to FIG. 1, an exemplary conebeam computed tomography (CT) scanner 10 includes an imaging subject support 12 such as a couch which is linearly movable along a Z-direction inside an examination region 14. An x-ray tube assembly 16 mounted on a rotating gantry projects x-rays through the examination region 14. A collimator 18 collimates the radiation in two dimensions. In the exemplary CT scanner 10, a two-dimensional x-ray detector array 20 is disposed on the rotating gantry across the examination region from the x-ray tube. In an alternative embodiment (not shown), the detector array includes an array of two-dimensional detector rings mounted on a stationary gantry around the rotating gantry.

The x-ray tube assembly 16 cooperates with the collimator 18 to produce a conical or wedge-shaped beam 22 (conebeam) which diverges conically as it passes through the examination region 14. The conebeam is shaped with a cross-section that substantially conforms to the 2D-detector array 20 with a minimum of overscan. The cross-section is rectangular, circular, or the like. Although a conebeam geometry is described herein, the invention is not limited thereto, but is also applicable to other CT geometries such as a fan-beam geometry which diverges in a plane as it passes through the examination region 14.

The cone beam 22 substantially covers the detector array 20, which in a suitable embodiment includes sixteen rows of 1–10 mm detector elements. It will be recognized that in the cone-beam geometry the x-ray paths to the various elements of the detector array 20 are not generally parallel, nor do they generally lie in a single plane. In the planar fan-beam geometry (not shown), the x-rays are not parallel but substantially lie in a single plane or in a plurality of planes corresponding to a plurality of detector rows.

Regardless of the detailed geometry of the x-ray beam 22 and the detector array 20, the x-ray detectors 20 operate in known ways to convert x-rays 22 that have traversed the examination region 14 into electrical signals indicative of x-ray absorption between the x-ray tube 16 and the detectors 20. The x-ray absorption signals, along with information on the angular position of the rotating gantry, the longitudinal position of the imaging subject support 12, and the detector element of the detector array 20, are communicated to a CT acquisition buffer memory 24. The data is typically organized into a projection data format of a type known to the art; however, those skilled in the art can select a suitable storage format for a particular CT embodiment.

An acquisition controller 26 communicates with the CT scanner 10 to control CT scanning of an imaging subject 28, such as a piece of luggage undergoing a security inspection or a patient undergoing a clinical computed tomography examination. In a suitable embodiment, an associated user selects appropriate CT scanning parameters or scan recipes using a user interface 32, which is typically a personal computer, workstation, or the like and which preferably includes graphical display capability and a graphical user interface (GUI). A typical helical CT scan includes helical orbiting of the x-ray source 16 about the imaging subject 28 effectuated by cooperative gantry rotation in an angular direction θ and linear movement of the imaging subject 28 in the Z-direction. The helical pitch is selected to provide at least 180° plus a fan beam angle of angular data for each volumetric element or voxel. In many imaging situations, it is preferable to acquire 360° or more of angular data for each voxel to provide redundant or complementary data. It will be appreciated that in the conebeam geometry, as the source rotates from an angular orientation of θ to an angular orientation of θ+n(180°) where n is an integer, the acquired projection data sampling a selected voxel are generally not coplanar because of the helical orbit and the conical divergence of the beam in the Z-direction.

The CT imaging apparatus optionally includes other elements for specialized clinical applications. For example, an electrocardiographic instrument (ECG) 36 can be included to monitor the cardiac cycling during cardiac CT imaging. The ECG 36 optionally communicates with the acquisition controller 26 to provide triggering for cardiac gated CT imaging or to provide cardiac phase information for post-processing a selected cardiac phase. A contrast agent administering means, such as a bolus injection syringe, is also optionally provided for performing contrast-enhanced CT imaging using an x-ray absorbing contrast agent 38. The ECG 36 and contrast agent 38 are exemplary auxiliary components; more, fewer, or other auxiliary apparatus can be incorporated into the clinical CT system.

With continuing reference to FIG. 1, the projection data stored in the acquisition buffer 24 is advantageously re-binned 50 with respect to the angular orientation θ to associate data having similar angular orientations. In a suitable embodiment, the re-binning 50 does not include sorting of angular deviations in the Z-direction. The re-binned data is stored in a re-binned projection data memory 52.

Reconstruction of conebeam projection data to form an image representation typically includes an enormous number of calculations. To accommodate these computational demands, an area of the image representation is advantageously divided 54 into a plurality of sub-matrices for subsequent processing.

Further computational efficiency is gained by distributing 56 the projection data into a plurality of parallel pipelines 60 for parallel computational processing. Depending upon the reconstruction geometry, spiral pitch, and other factors, it can be desirable to combine complementary or redundant data angularly separated by one or more half rotations of the x-ray source 16. Such data is separated by one or more half-cycles, or in other words the data are angularly congruent modulo 180°. Typically, such data is advantageously combined through a weighted summation of the complementary or redundant projection data which is separated by one or more half-cycles.

To support selective combination of complementary or redundant projection data, a plurality of reconstruction pipelines are grouped into groups of four pipelines each. In FIG. 1, a control word 58 controls combination of an exemplary group of four pipelines 60. Typically, the reconstruction apparatus will include a number of such groups of four pipelines 60, each having an associated control word 58. Based upon the value of the control word 58, each of the pipelines 60 processes projection data independently; or two, three, or four of the pipelines 60 cooperatively process and combine complementary or redundant projection data from neighboring half-cycles. The contents of the control word 58 decide if and which selected pipelines are to be combined. Each pipeline 60 applies appropriate filtering, angular weighting W given by W(θ), and detector aperture weighting G given by G(Z).

For a reconstruction in which the control word 58 directs cooperative reconstruction processing by two or more pipelines 60, the combined weightings WG of the grouped pipelines are applied to the projection data to produce weighted projection data. The weighted projection data for neighboring half-cycles processed in the parallel pipelines 60 is additively combined and normalized 62 by the weighting elements WG to produce weighted sub-matrix projection data $P_{out}$ 64.

Pipelines 60 which are operating independently typically employ no weighting: W=1, G=1, and the combined weighting WG=1. It will be appreciated that the group of pipelines 60 produce four distinct parallel projection data outputs $P_{out}$ 64 when the four pipelines are acting independently. If two pipelines are acting cooperatively then three distinct parallel projection data outputs $P_{out}$ 64 are produced. If three pipelines are acting cooperatively then two distinct parallel projection data outputs $P_{out}$ 64 are produced. If all four pipelines are acting cooperatively then a single distinct projection data output $P_{out}$ 64 is produced. The control word 58 determines how the pipelines 60 are combined.

In a preferred embodiment, it was found that an optimal grouping of pipelines 60 is four pipelines in each group, which provides significant computational gains and flexibility in combining neighboring half-cycles while limiting the data combining to four neighboring half-cycles to restrict angular variation of the combined data in the Z-direction. of course, pipelines can be arranged with greater or fewer than four pipelines in each group. It will also be appreciated that there are typically a number of groups. For example, sixty four pipelines are suitably arranged into sixteen groups of four pipelines each, with FIG. 1 showing only an exemplary one group of four pipelines.

The weighted projection data for each sub-matrix is back-projected 66 or otherwise reconstructed to produce a sub-matrix image representation that is stored in a sub-matrix image memory 68. The plurality of sub-matrix image representations so obtained are combined to form a complete image reconstruction which is stored in a volume image memory 70.

It will be appreciated by those skilled in the art that the selected sub-matrices 54 need not all lie in a single plane. For example, the sub-matrices can "spiral" along with the helical data acquisition so that each sub-matrix is well-centered within the detector aperture. Moreover, the sub-matrices need not lie perpendicular to the Z-direction. Sub-matrices can be selected to provide an optimized slice orientation or to align with a non-standard CT data acquisition geometry. It is also contemplated to select non-parallel sub-matrices, for example to optimally reconstruct selected areas of clinical interest. The sub-matrices can be rectangular sub-matrices, thin cubic sub-matrices, hexagonal sub-matrices, or the like.

A selected real-space or volume sub-matrix will have a corresponding sub-matrix in projection space. This advantageously improves reconstruction processing data flow, because during reconstruction of a selected volume sub-matrix only a sub-set of the projection data containing those projections which contribute to the volume sub-matrix need to be loaded into memory.

The obtained image representation is preferably rendered into an appropriate clinical image, such as a maximum intensity projection (MIP), a three-dimensional rendering, or a gray scale or color-coded image of a selected two-dimensional image slice, by a graphical rendering processor 72. The resulting image is displayed on the graphical user interface 32 for examination by the CT operator, is optionally printed, stored on a magnetic or optical storage medium, transferred via an associated computer network, or the like.

The embodiment illustrated in FIG. 1 is exemplary only. Those skilled in the art can make suitable modifications to suit individual situations. For example, in one suitable apparatus the sub-matrices allocation 54, data distribution 56, pipelines 60, summer/normalizer 62, and backprojector 66 are embodied by an application-specific integrated circuit (ASIC) that communicates with one or more data memory units. In another suitable apparatus, the user interface 32 includes a workstation, personal computer, or similar general-purpose computing device having data storage devices that embody the data memories 52, 64, 68, 70, and software that embodies one or more of the processing elements 50, 54, 56, 60, 62, 66. In yet another suitable embodiment, one or more of the processing elements 50, 54, 56, 60, 62, 66 are embodied as a set of computer instructions of a software program that are stored on a magnetic disk, optical disk, or other storage element.

Figure 2:
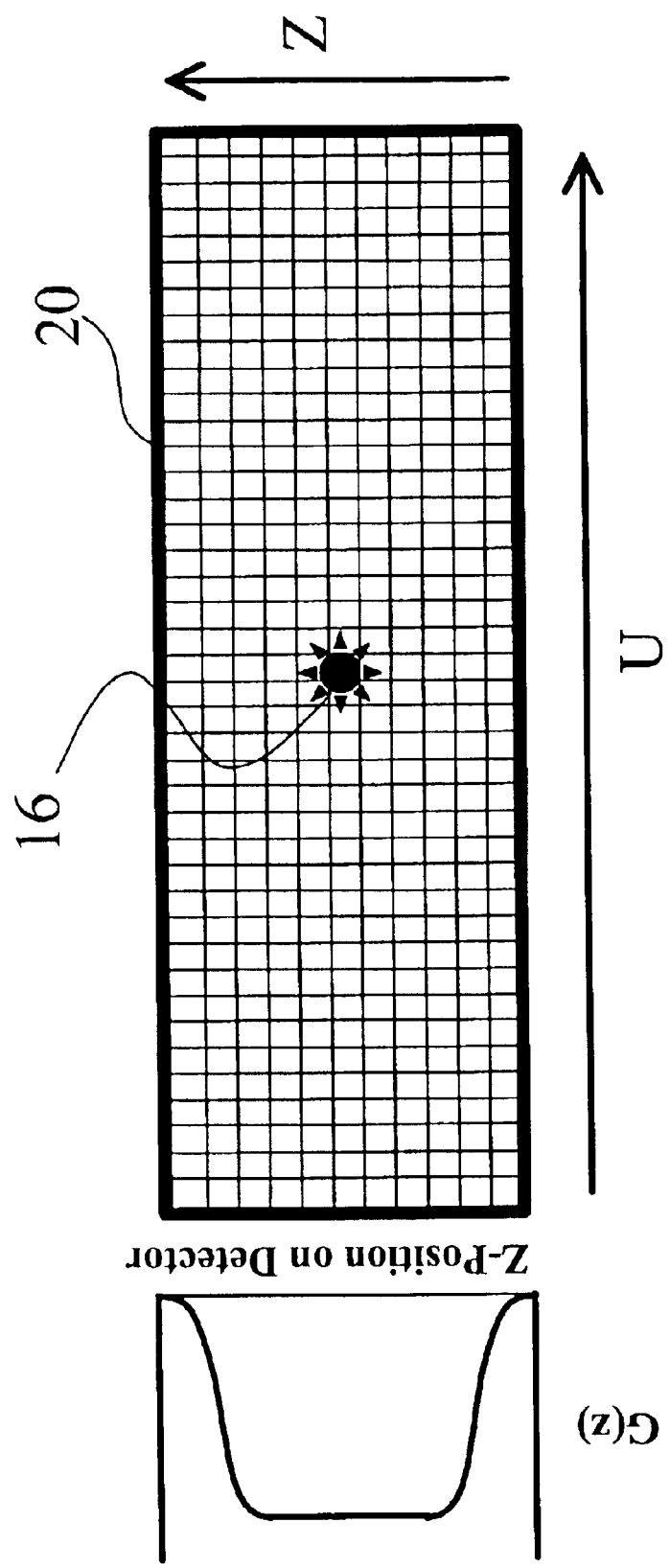
FIG. 2 shows a view of the two-dimensional detector array of the CT system of FIG. 1 looking from behind the x-ray source whose location relative to the extent of the detector array is schematically represented.

With continuing reference to FIG. 1 and with further reference to FIG. 2, a suitable coordinate system for the reconstruction is described. FIG. 2 shows a view of the detector array 20 looking from behind the source 16. For a given projection viewing a sub-matrix made up of voxels $V(x,y,z)$, the detector having association with a selected voxel is located on a line originating at the x-ray source 16 and passing through the coordinate $(x,y,z)$ of the selected voxel. As seen in FIG. 2, the detector elements are indexed by a $(U,Z)$ coordinate system. U corresponds with the detector pixel and Z corresponds with the detector row. The $(U,V,Z)$ coordinate system is a rotating coordinate system associated with the rotating x-ray source 16. The V coordinate is orthogonal to both the U and Z coordinates, so that the $(U,V,Z)$ coordinate system forms a rotating orthonormal coordinate system.

Each voxel $V(x,y,z)$ is associated with a plurality of projections having a range of angular orientations and corresponding detector coordinates. Hence, as the reconstruction algorithm successively backprojects the voxels of a sub-matrix, a relationship between $(U,z)$ and $(x,y,z)$ is employed.

With continuing reference to FIG. 2, the detector coordinate $U(x,y)$ of the voxel $V(x,y,z)$ is estimated in linear fashion according to:

$$U = U_0 + U_{10}x \quad (1)$$

where $$U_0 = U_{00} + U_{01}y \quad (2)$$

and where $U_{00}$, $U_{01}$, and $U_{10}$ are constants. The linear relationship of equations (1) and (2) hold well for a uniform gantry rotation rate and a sub-matrix oriented perpendicular to the Z-direction. More complex relationships can be employed for more complex geometries and source orbits.

The variation in detector row Z is non-linear even for a uniform rotation and uniform linear movement of the subject 16, due to the helical nature of the rotation. In a preferred embodiment, a parabolic approximation $Z(x,y)$ is used:

$$Z = Z_0 + Z_1 x + Z_2 x^2 \quad (3)$$

where $$Z_0 = Z_{00} + Z_{01}Y + Z_{02}y^2 \quad (4),$$

$$Z_1 = Z_{10} + Z_{11}Y + Z_{12}y^2 \quad (5),$$

$$Z_2 = Z_{20} + Z_{21}Y + Z_{22}Y^2 \quad (6),$$

and $Z_{00}$, $Z_{01}$, $Z_{02}$, $Z_{10}$, $Z_{11}$, $Z_{12}$, $Z_{20}$, $Z_{21}$, and $Z_{22}$ are constants. The use of a non-linear relationship for the Z detector row index allows for more accurate reconstruction of images acquired with larger cone angles and using larger sub-matrices compared with a linear Z detector row index calculation. More elaborate Z approximations can be employed at the cost of longer computing times.

A suitable image reconstruction of a selected sub-matrix is described by the expression:

$$V(x,y,z) = \sum_{n=1}^{N} \left[ \sum_{m=1}^{M} \frac{W_n G_m P_{n,m}}{\sum_{m'=1}^{M} W_n G_{m'}} \right] = \sum_{n=1}^{N} P_{out} \quad (7)$$

where the index m, m' running from 1 to M references the pipeline identifier which corresponds to the data half-cycle, the index n running from 1 to N references the re-binned projection viewing angle $\theta$, $P_{n,m}$ is the mth re-binned projection at the angle referenced by n, $W_n$ is the angular orientation weighting W corresponding to the angle $\theta_n$, $G_m$ is the detector aperture G weighting for the detector row corresponding to the mth half-cycle, $P_{out}$ is the weighted sub-matrix projection data $P_{out}$ 64 shown in FIG. 1, and $V(x,y,z)$ is the backprojected value for the volume element or voxel at $(x,y,z)$ which is being calculated.

The weighting functions W, G given by $W(\theta)$ and $G(Z)$ are selectable to correct for various artifacts or other image degradation mechanisms associated with the imaging modality and the imaging geometry of the projection data being reconstructed. For example, in spiral fan-beam wedge image reconstructions, the angular weighting $W(\theta)$ is preferably set to $W(\theta)=1$ so that only detector aperture weighting is applied. The detector aperture weighting $G(Z)$ is selected to reduce artifacts resulting from beam divergence in the Z direction, enabling greater use of the detector array 20. For half-pitch spiral fan-beam wedge reconstructions, use of the entire detector is particularly advantageous for achieving low noise imaging. The combination of several half-cycles using the pipelines 60 also improves the signal to noise ratio.

For axial reconstructions, the angular weighting $W(\theta)$ is selected to achieve improved temporal resolution. Using a 360° cosine angular weighting for $w(\theta)$ is advantageous for this type of reconstruction. Similarly, for cardiac imaging appropriate angular weighting $W(\theta)$ can be applied to the gated data set portions to obtain high temporal resolution.

For continuous volume CT imaging, weightings $G(Z)$ and $W(\theta)$ are preferably both set to unity, and data is extrapolated beyond the detector aperture as necessary.

Those skilled in the art will be able to select weighting functions $w(\theta)$ and $G(Z)$ to improve image characteristics under other imaging geometries and modalities.

An advantage of the $G(Z)$ weighting function is that it provides a mechanism for defining a "virtual" aperture which does not coincide the "physical" aperture defined by the extent of the detector array. The aperture function $G(Z)$ is optionally used to define a virtual aperture that provides improved smoothing or is accommodates a selected CT imaging mode.

Figure 3:
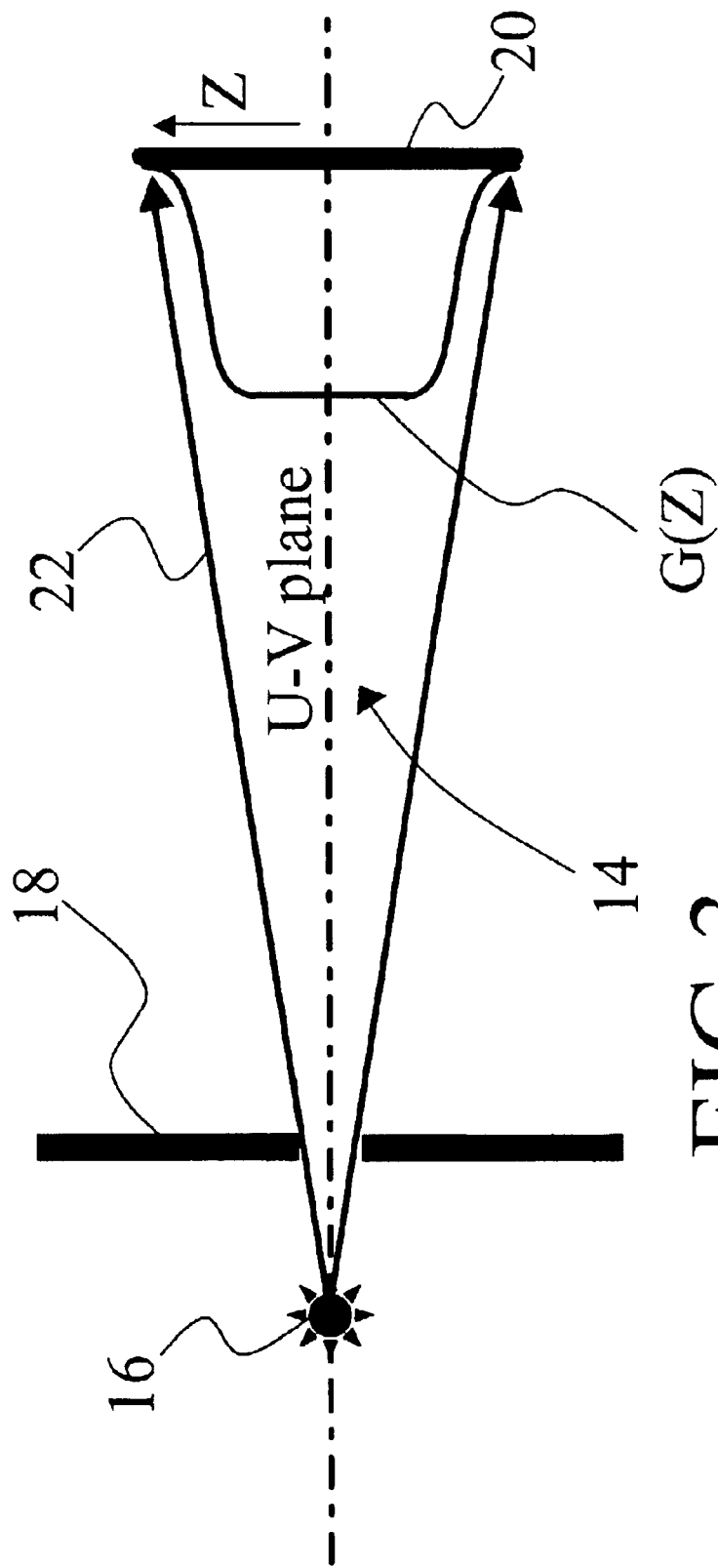
FIG. 3 schematically shows a CT geometry relating the source, detector, detector aperture function G(Z), and the rotating (U,V,Z) coordinates.

With continuing reference to FIG. 2 and with further reference to FIG. 3, the aperture weighting function $G(Z)$ decreases toward zero near the edges of the aperture 20. In reconstructions in which angularly redundant data is combined using two or more pipelines 60 under direction of the control word 58, this gradual decrease of the aperture weighting function $G(Z)$ beneficially reduces an amplitude of data acquired near the aperture edge to provide a smooth transition for redundant data. The 50% dropoff point of the edges of G(Z) are selected to balance artifacts due to a sharp cutoff with reduction in the virtual aperture size which results from a more gradual drop-off of G(Z).

Figure 4:
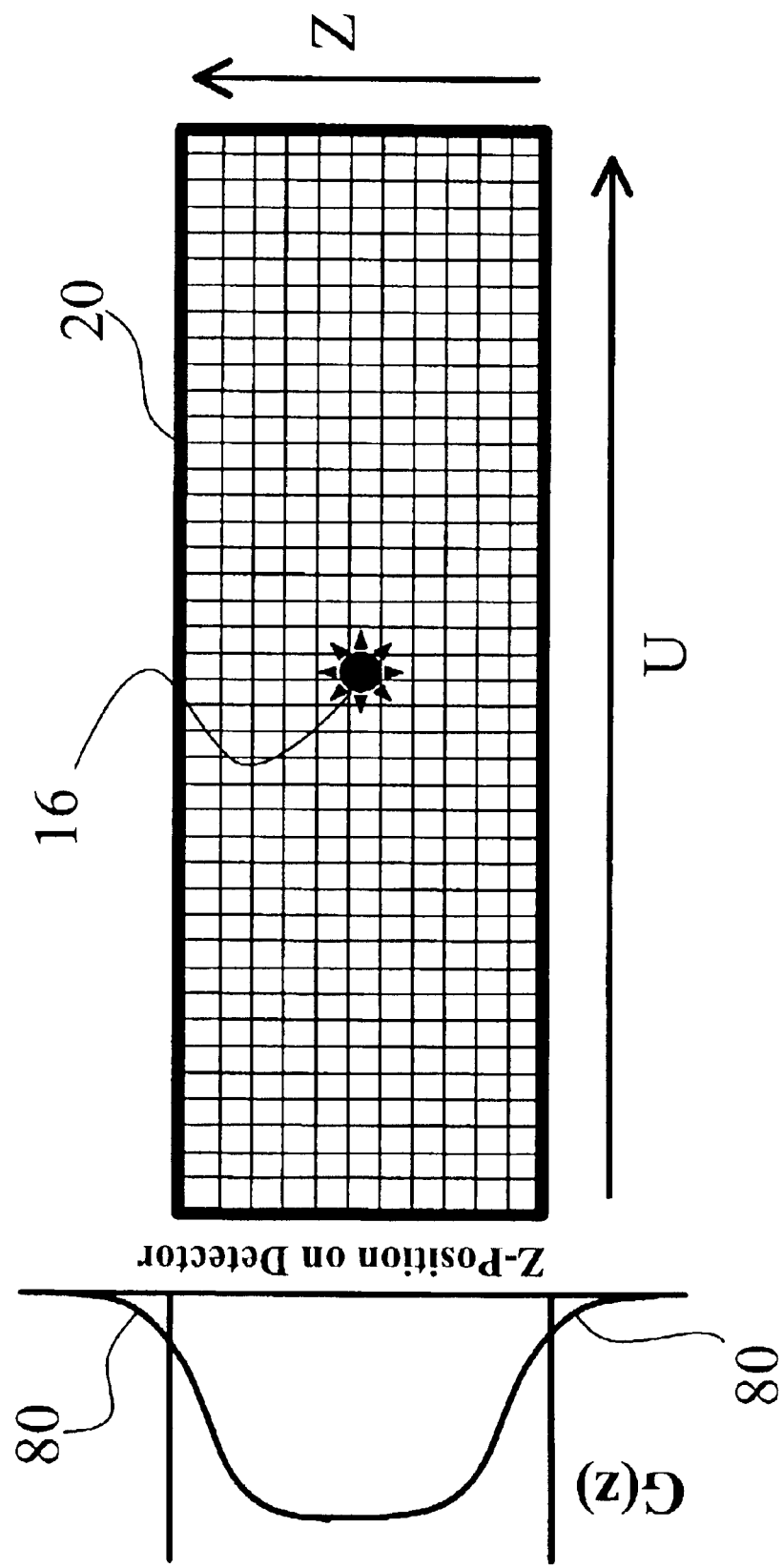
FIG. 4 shows an aperture function G(Z) that extends beyond the physical aperture to define a virtual aperture that is wider than the detector array.

With reference to FIG. 4, the weighting function G(Z) is optionally selected to be greater than the size of the physical aperture 20. The 50% dropoff points of the aperture function G(Z) preferably remain at the same Z positions and the aperture weighting function G(Z) is spread out. The spread-out weighting function G(Z) includes portions 80 lying outside the physical aperture which have no corresponding measured projection data. In the outside portions 80 of the virtual aperture, projection data at the nearest edge of the physical aperture 20 are extrapolated.

The weighting function G(Z) of FIG. 4 is seen to define a virtual aperture which is larger than the physical aperture 20 due to the extrapolated regions 80. The weighting function of FIG. 4 provides an enlarged field of view compared with the physical aperture 20. Although the edges of the enlarged field of view may contain artifacts due to the extrapolated portions 80, such artifacts are generally less severe than truncation artifacts produced by a sharp aperture cutoff.

Figure 5:
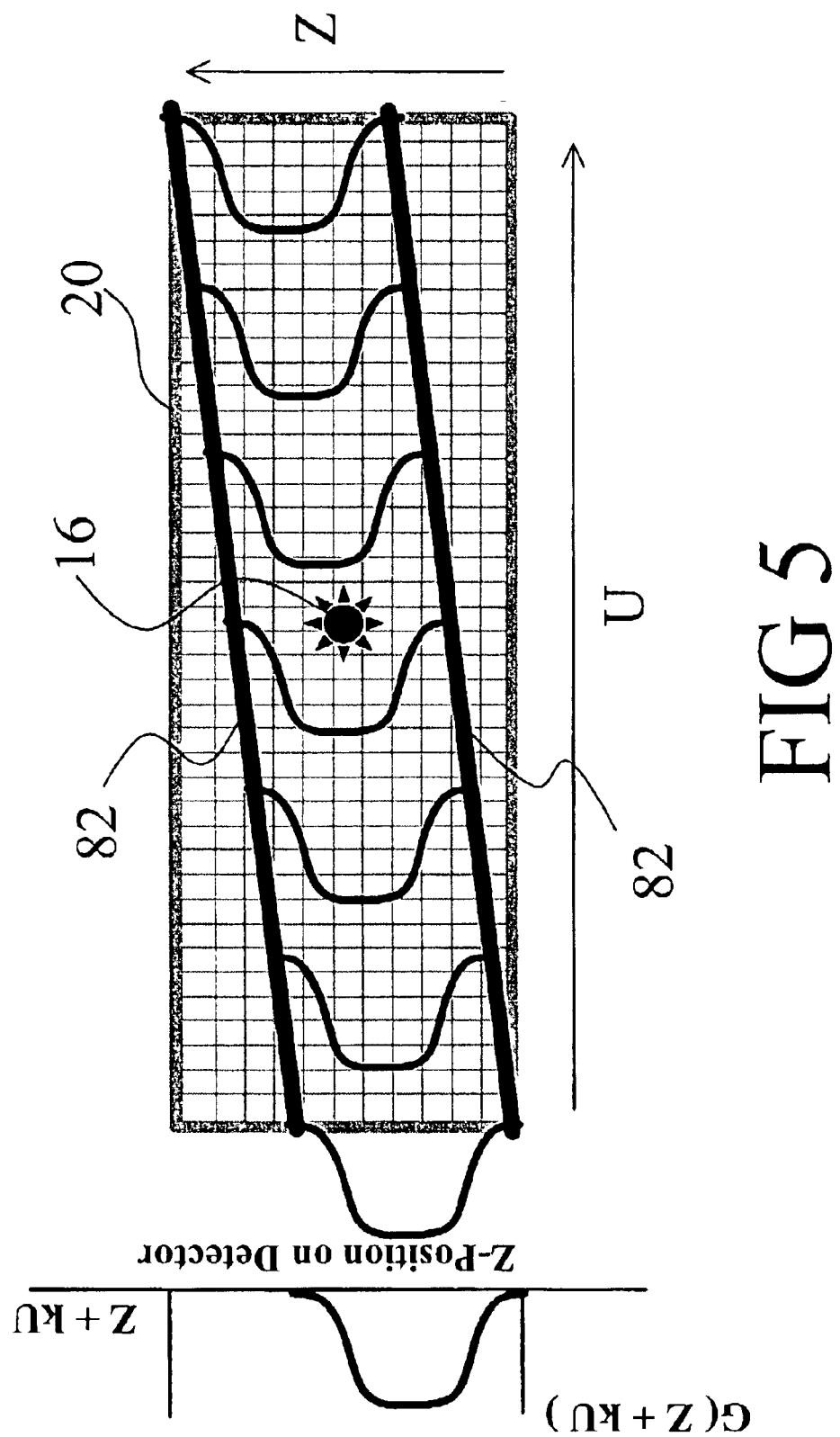
FIG. 5 shows an aperture function G(Z+kU) that defines a virtual aperture with slanted edges for improved correspondence with helical CT image data acquisition.

With reference to FIG. 5, yet another aperture function G is described, in which the functional z dependence is replaced by a Z+kU dependence, i.e. the weighting function G(Z) is replaced by the weighting function G(Z+kU), where k is a constant, so that the aperture weighting depends upon both the Z and the U coordinates. As seen in FIG. 5, a linear U dependence of the aperture function, G(Z+kU), produces a virtual aperture having slanted edges 82. The slanted-edge virtual aperture defined by the aperture function G(Z+kU) is particularly suitable for helical CT imaging, where the slant of the slanted edges 82 are selected to correspond with the pitch of the helical orbiting of the x-ray source 16. Of course, other U-dependences can also be used to suitably match parabolic, tangential, or otherwise-shaped edges of the projection data of interest. In a suitable construction, the slanted virtual aperture of FIG. 5 is obtained by rebinning of the U-dependent addressing using the rebinning processor 50.

The virtual aperture can also be selected to match a selected x-ray beam collimation. For example, it is contemplated to employ a collimation system which collimates the beam into a rectangular or other cross-sectional shape. The virtual aperture is preferably selected to match a distribution of the shaped x-ray beam on the physical aperture 20.

Figure 6A:
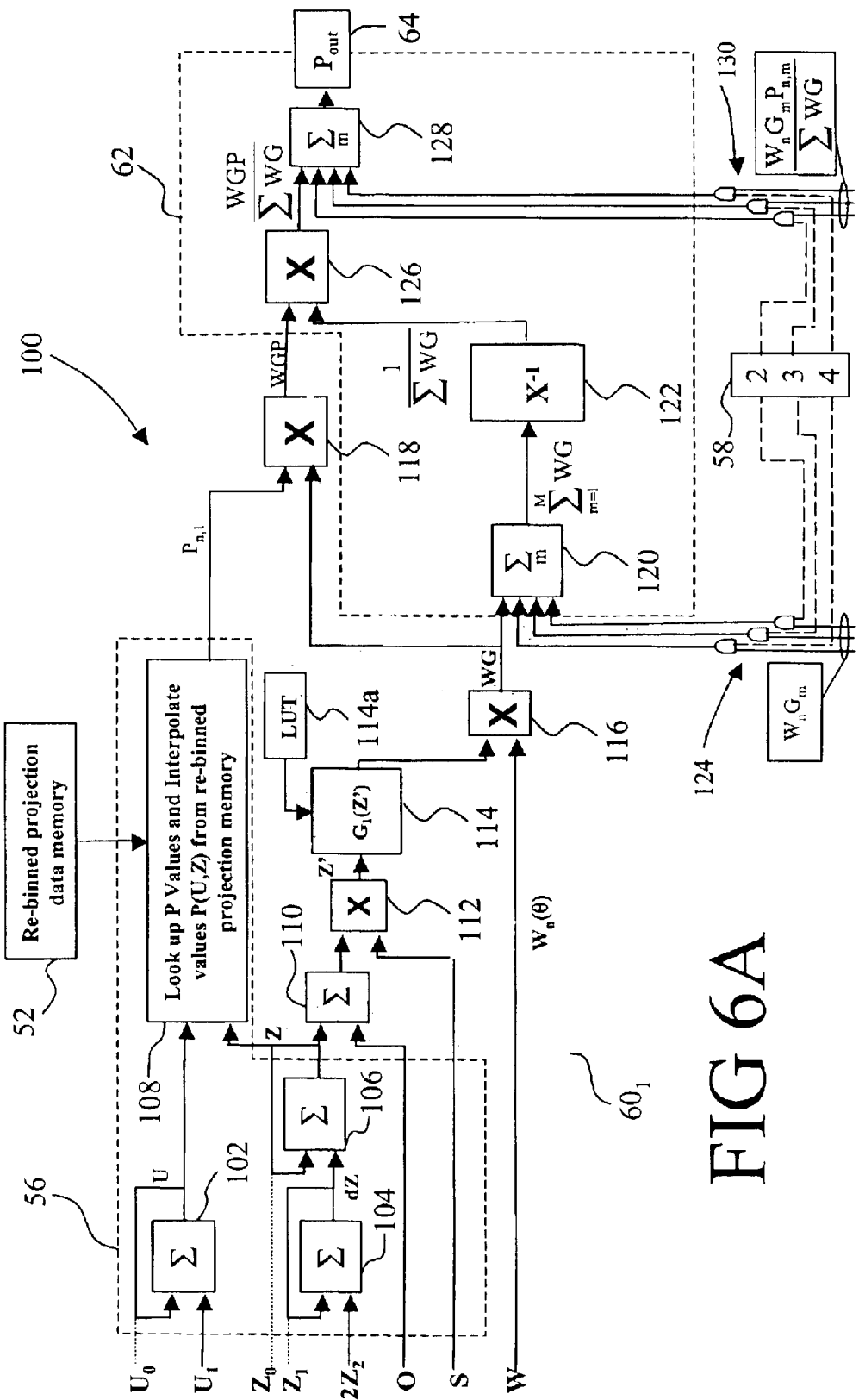
FIG. 6A shows an exemplary portion of a processing pipeline for weighting and combining projection data that suitably practices an embodiment of the invention.

With returning reference to FIG. 1 and with further reference to FIG. 6A, a method 100 for selectively combining complementary or redundant projection data in weighted fashion (that is, for computing the $P_{out}$ term of equation (7)) is described. FIG. 6A shows an exemplary pipeline $60_1$ (pipeline index m=1) selected from the pipelines 60 along with a suitable voxel distribution processing 56 and the sum/normalize block 62 of FIG. 1. Referencing FIG. 6A, the constants $U_0$, $U_1$, $V_0$, $V_1$, $Z_0$, $Z_1$, and $Z_2$ are obtained for a selected sub-matrix 54 (FIG. 1) and angular orientation. The distribution processor 56 cycles through the spatial coordinates of the sub-matrix. A summer 102 recursively calculates the U coordinate according to equations (1) and (2), while summers 104, 106 recursively calculate the Z coordinate according to equations (3)–(6). Using the (U,Z) coordinates, an appropriate projection value is interpolated and retrieved 108 from the re-binned projection memory 52. In a suitable embodiment, a two-dimensional linear interpolation of the projection data is used. Linear interpolation in the step 108 is adequate if the data is preprocessed, for example by. filtering or by pre-interpolating.

Based on the value of the Z coordinate, optionally adjusted by a linear offset 110 and/or a scaling factor 112, an aperture weighting G is selected in a step 114. The linear offset and scaling 110, 112 allow the aperture to follow a set of slanted edges or π lines without requiring additional re-binning of the 2D projection data. Exemplary detector aperture weighting functions are shown in FIGS. 2–5. In a suitable embodiment, the aperture weighting value is obtained from a lookup table 114a.

The selected aperture weighting G 114 is multiplied in a step 116 by an angular weighting $W_n(\theta)$ to produce the combined weighting factor WG. The angular weighting $W_n(\theta)$ is optionally obtained from a lookup table. The combined weighting factor WG is multiplicatively applied 118 to the projection value to produce a weighted projection value WGP. However, this weighted projection value WGP has not been selectively normalized and combined with the outputs of the other pipelines, if such combination is called for based on the control word 58.

A normalization factor is calculated by a summing step 120 which selectively sums the weighting factors $W_n G_m$ of each pipeline $60_m$ and inverts the sum in an inverting step 122. The selective summation is controlled by the control word 58 through a selection circuit 124 that selectively gates the weighting factors $W_n G_m$ of the three additional pipelines m=2, m=3, and m=4 based on contents of the control word 58.

Figure 7:
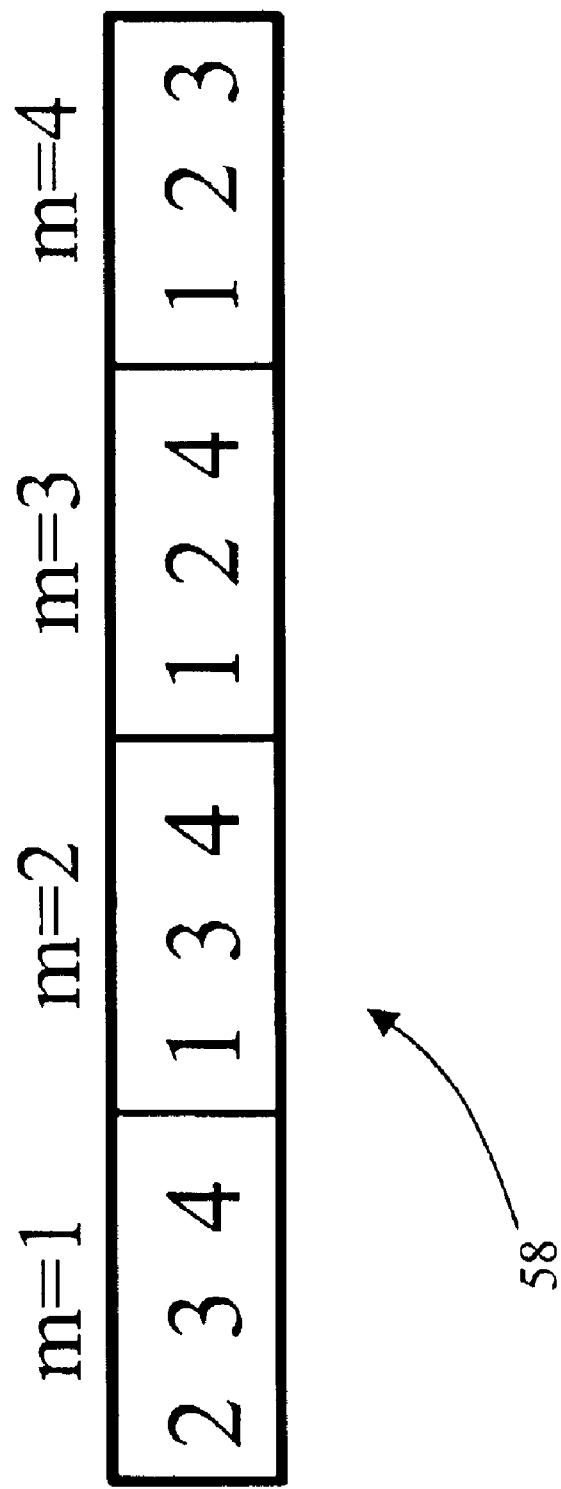
FIG. 7 diagrammatically shows a suitable twelve-bit control word for controlling selective combination of pipelines of a group of four pipelines for selective parallel combination of complementary or redundant projection data.

With reference to FIG. 7, for a four pipeline grouping a suitable control word 58 is a twelve bit value containing three control bits for each pipeline m. The three control bits corresponding to each pipeline identify which, if any, of the other pipelines should be combined with that pipeline. For the illustrated m=1 pipeline $60_1$ the control word has three control bits (the leftmost three control bits in FIG. 7) corresponding to the neighboring pipelines m=2, m=3, and m=4. A binary one ("1") corresponding to a neighboring pipeline causes that pipeline to be combined with the m=1 pipeline. Hence, if the control word 58 contains control bits "111" for the pipeline $60_1$ then all three neighboring pipelines $60_2$, $60_3$, $60_4$ are combined with the output of pipeline $60_1$. If, however, the control word 58 contains control bits "000" for the pipeline $60_1$ then no other pipeline output is combined with the output of pipeline $60_1$. To provide one further example, if the control word 58 contains control bits "010" for the pipeline $60_1$ then only the m=3 pipeline output is combined with the output of pipeline $60_1$.

As seen in FIG. 7, the pipeline m=2 similarly has three control bits corresponding to the neighboring pipelines m=1, m=3, and m=4. The pipeline m=3 has three control bits corresponding to the neighboring pipelines m=1, m=2, and m=4. The pipeline m=4 has three control bits corresponding to the neighboring pipelines m=1, m=2, and m=3.

With returning reference to FIG. 6, to implement selective combining of zero, one, two, or three other pipelines $60_m$ with the pipeline $60_1$ using the first three control bits designated "234" of the control word 58, the exemplary selection circuit 124 includes three input gates corresponding to the three additional pipelines m=2, m=3, m=4. Each input gate passes the corresponding weighting factor $W_n G_m$ to the summation block 120 if the control word 58 includes a bit value one (1) for that pipeline.

Symmetry among the four pipelines $60_m$ is maintained in that: the summation block for the m=2 pipeline selectively gates the m=1, m=3, and m=4 pipeline weighting factors $W_n G_m$; the summation block for the m=3 pipeline selectively gates the m=1, m=2, and m=4 pipeline weighting factors $W_n G_m$; and the summation block for the m=4 pipeline selectively gates the m=1, m=2, and m=3 pipeline weighting factors $W_n G_m$.

The normalization factor is applied to the weighted projection value WGP in a multiplicative step 126. At a summation block 128, the normalized outputs of is the pipelines selected by the control word 58 are combined through a second selection circuit 130 which is functionally similar to the selection circuit 124. The output of the summation block 128 is $P_{out}$ 64 which sums the weighted and normalized contributions from the m=1 pipeline and any additional selected combined pipelines.

The control word 58 and corresponding selection circuits 124, 130 are exemplary only. Those skilled in the art can readily construct other selection control elements using various combinations of gates, storage registers, and the like. Moreover, the selective combination machinery 58, 124, 130 is readily adapted to accommodate greater or fewer than four pipelines.

Figure 6B:
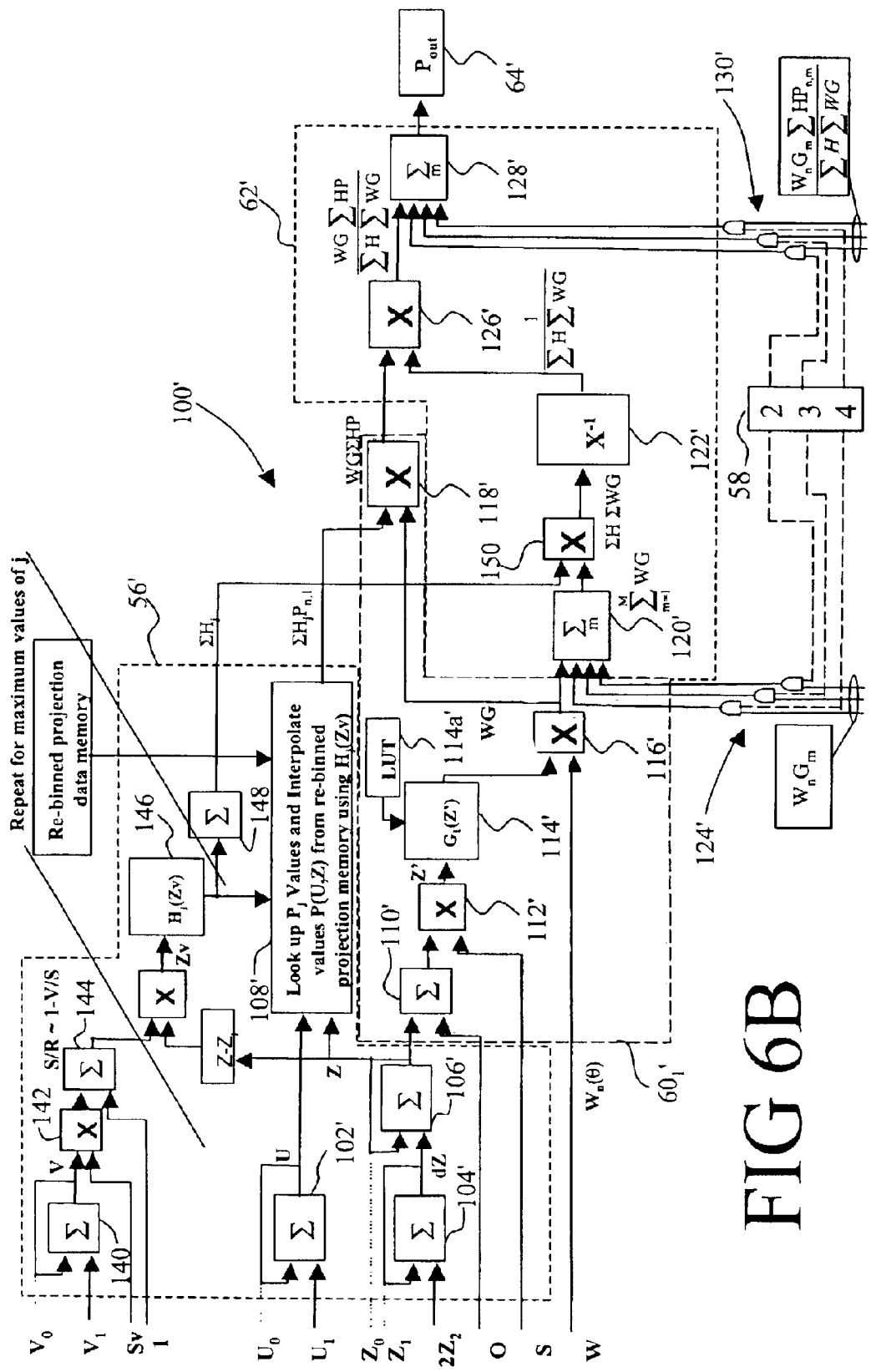
FIG. 6B shows the pipeline of FIG. 6A with additional components for performing spatially uniform projection interpolation along the axial or Z-direction.
Figure 8:
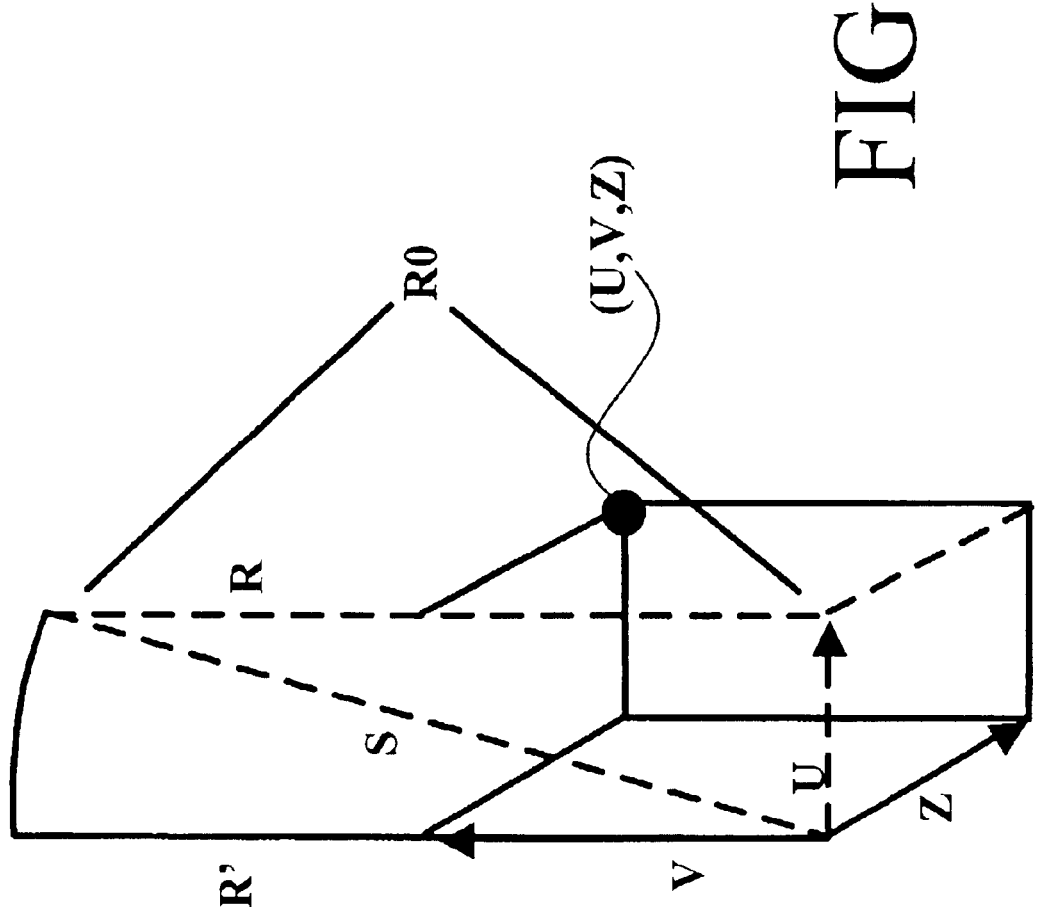
FIG. 8 diagrammatically shows geometry and coordinates for performing spatially uniform projection data interpolation along the Z-direction.

With reference to FIG. 6B and with further reference to FIG. 8, the method 100 is modified to include a spatially uniform projection interpolation in the Z-coordinate direction. FIG. 6B shows a method 100' which is substantially similar to the method 100 of FIG. 6A, except for inclusion of spatially uniform projection interpolation in the Z-coordinate direction. In FIG. 6B, components of the method 100' which have corresponding steps in the method 100 are designated by corresponding primed reference numbers.

It will be recognized that even with angular rebinning the projections are not fully parallel but rather include angular variance respective to the U-V plane (see FIG. 3). This angular divergence, if left uncorrected, results in a non-uniform projection interpolation which varies with the V-coordinate, i.e. with distance relative to the x-ray source or distance relative to the detector. Preferably, a look-up table H[ ] is used to correct for the angular divergence respective to the U-V plane. In a preferred embodiment, the P(U,Z) projection value is obtained from the projection memory 108 using:

$$\Sigma H[Z_v] = \Sigma H[(Z-Z_j)*(S/R)] \qquad (8)$$

where H[ ] is a look-up table whose spatial width is typically about 1.3 times the detector width in the Z-direction, $Z_j$ are the projection data row locations nearest to Z, S is the source radius, $$S/R = 1/(R_0 + V/S) \approx S/R' = 1/(1+V/S) \approx (1-V/S) \qquad (9)$$

V is the voxel address in the vertical dimension of the rotating plane, and $R_0[U] = \sqrt{1-(U/S)^2}$, which however drops out in the approximation of equation (9).

With continuing reference to FIGS. 6 and 8, the spatially-uniform projection interpolation along the Z-direction described in equations (8) and (9) is implemented in the method 100' of FIG. 6B by a summer 140, multiplier 142, and second summer 144 that compute S/R according to equation (9), and a look-up table H[ ] 146 that is accessed according to equation (8). The interpolation is performed over several $Z_j$ coordinates within the width of H[ ], which is typically about 1.3 times the width in the Z-direction of the physical aperture of the detector array 20. The weighting factors extracted from the lookup table H[ ] 146 and applied are accumulated at a summation block 148, and the cumulative weighting is multiplicatively incorporated into the normalization factor at a multiplication block 150.

For fan-beam CT, a distance weighting is optionally applied rather than re-binning the data to correct for the fan-beam angular divergence. The pipeline 100' of FIG. 6B is readily modified to accommodate fan beam distance weighting by a factor of S/R since this weighting factor is available as the output of summer 144.

Those skilled in the art will recognize many advantages of the pipelines 100, 100'. By selecting an appropriate value for the control word 58, the four pipelines $60_1$ can process projection data independently, or can be selectively combined in any manner. For example, the pipelines $60_1$ and $60_2$ can be used to combine two neighboring half-cycles, while the pipelines $60_3$ and $60_4$ can be used to independently combine two other neighboring half-cycles. By changing the value of the control word 58, all four pipelines $60_m$ can be combined, or all four pipelines $60_1$ can be operated independently, or another selected pipeline combination or combinations can be implemented. Moreover, the pipelines 100, 100' are readily adapted to groupings with more or fewer than four channels by expanding the size of the control word 58 and adding input gates to the selection circuits 124, 130 or to the selection circuits 124', 130', respectively.

The disclosed three-dimensional reconstruction provides an expandable architecture which is applicable to a wide range of CT imaging modes by proper selection of the weighting factors $W(\theta)$ and $G(Z)$, and proper selective combination of neighboring pipelines under direction of the control word 58. Such combining can be dynamically changed during image reconstruction by modifying contents of the control word 58.

The method also facilitates combining acquired half-cycles, for example to appropriately combine overscan regions by using symmetric normalized angular weightings applied to the overscan regions. The use of sub-matrices has provides further advantages including requiring fewer rows stored in random access memory, reduced computational load, and smaller ranges in the Z-direction over which the non-linear approximation of equations (3)–(6) is applied.

These features are also advantageous for optimally weighting and combining data acquired during gated imaging or modulated dose imaging. Appropriate weighting values $W(\theta)$ are selected to provide a feathering of the data near the angular boundaries of data acquisition to facilitate joining of angularly adjacent projection data portions.

Figure 9:
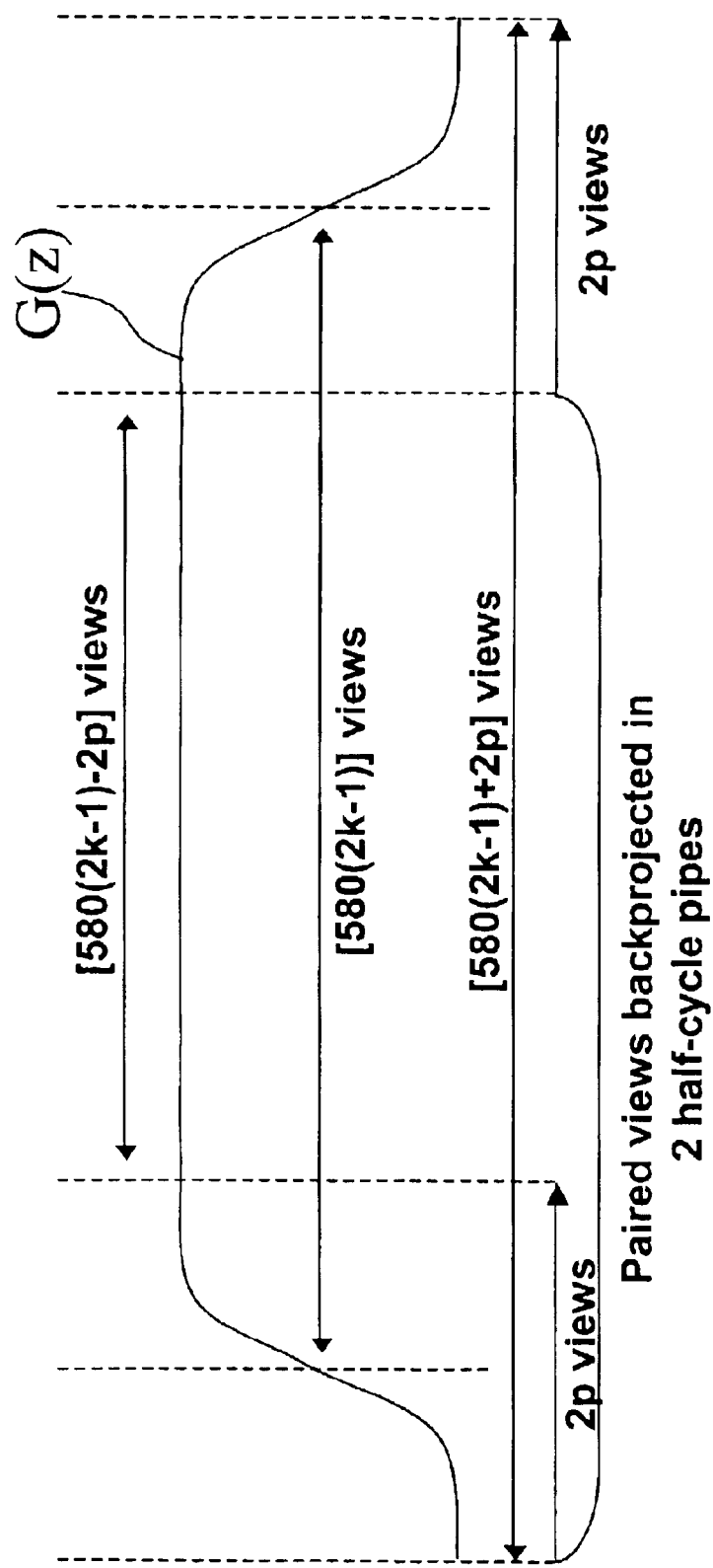
FIG. 9 illustrates an exemplary k–π reconstructions of a "(2k−1)π plus" angular range where k is an integer index.

With particular reference to FIGS. 1 and 6A, and with further reference to FIG. 9, a suitable method for handling an exemplary k–π reconstructions of a "(2k–1)π plus" angular range (where k is an integer index) is described. In this example, the plus angular range for any reconstructed voxel is less than ±p views. G(Z) is set forth in a lookup table and includes a flat region (G(Z)=1) except near the ends, which correspond to a plus range less than ±p views for any voxel. To provide a quantitative example, backprojection of a total of views equal to [580(2k–1)+2p] for 1160 views per revolution is described.

The first and last 2p views are backprojected using two half-cycle pipelines 60 that share a normalization 120. For example, pipelines $60_1$, $60_2$ can be used for the combining through selection by the control word 58. For these backprojections, the angular weighting factor $W(\theta)$ is set to unity for both pipes. However, because the same number of views are being backprojected for all voxels, some views will "fall off the detector aperture". This is accommodated in the weighting 118 by the aperture weighting component G(Z) which goes to zero for those out-of-aperture views.

In a case where k=1, such as in a wedge reconstruction, (2k–1)π corresponds to a 180° angular range and the reconstruction is done if p≧290 so that p views cover at least a 90° angular range. In a case where k≧1 or p≦290, the remaining

[580(2k−1)−2p] views are reconstructed using independent pipelines with weighing values of W(θ)=1 and G(Z)=1. These independent reconstructions can be processed simultaneously with the combined reconstruction of pipelines $60_1$, $60_2$ by using one or both of the remaining two pipelines $60_3$, $60_4$ operating independently of the other pipelines.

Finally, since now the (2k−1) half-cycles of data have been effectively backprojected, the images or the projections are scaled by 1/(2k−1) to obtain the correct overall normalized result. This will naturally flow from the normalizing blocks 120, 122 of FIG. 6A since WG=1 for all (2k−1) views.

Figure 10A:
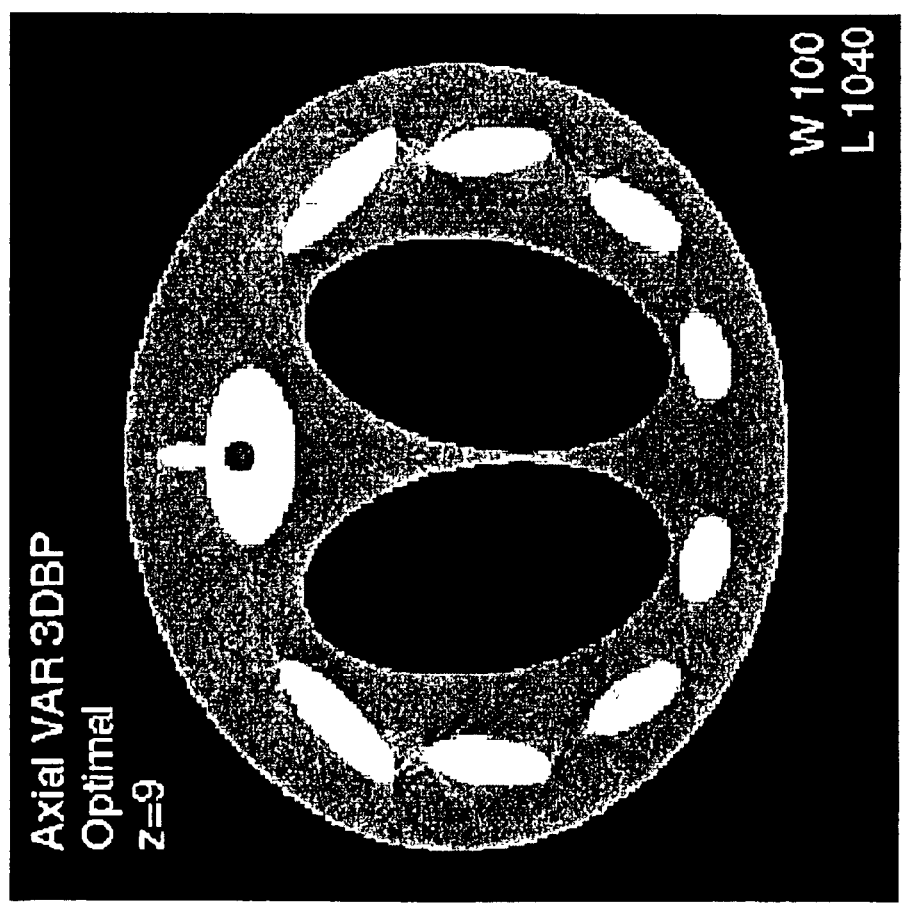
FIG. 10A shows exemplary results for imaging of a three-dimensional "rib-lung" phantom at z=9 mm in accordance with a suitable embodiment of the invention using variable angular weighting based on the detector aperture function.
Figure 10B:
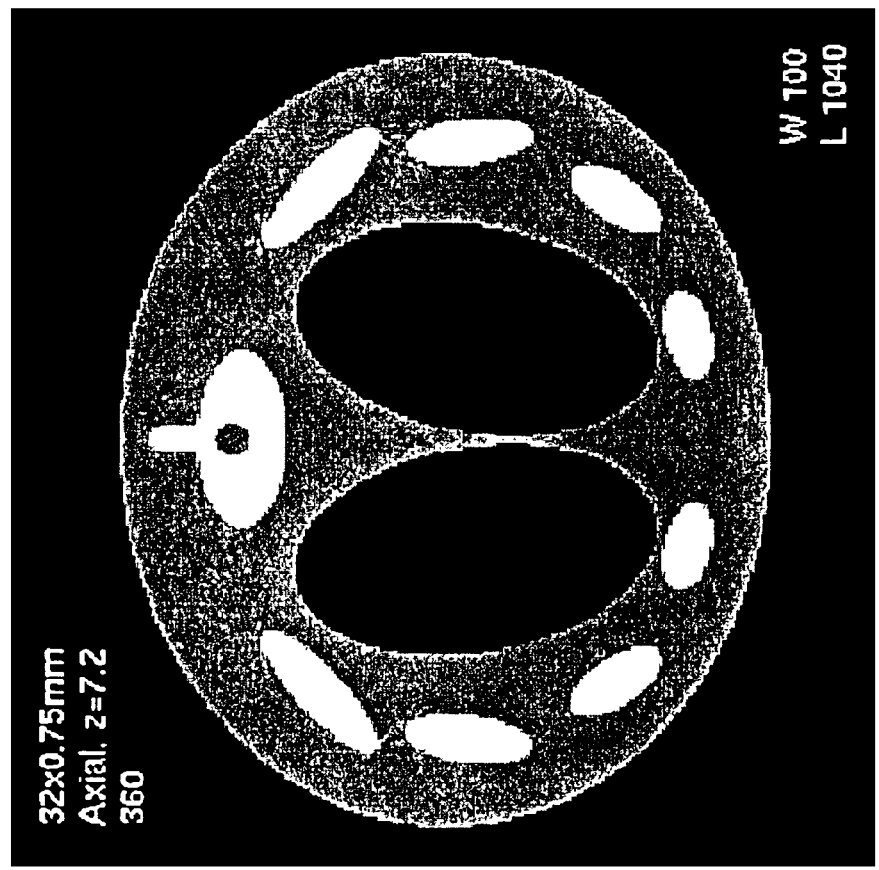
FIG. 10B shows a prior art 360° reconstruction at z=7.2 mm, for comparison with the image of FIG. 5A (The prior art 360° reconstruction is possible only for a z position up to 7.2 mm).

With reference to FIGS. 10A and 10B, exemplary results for imaging of a three-dimensional "rib-lung" phantom is shown. The 'ribs' of the phantom are oriented in three-dimensions to provide a severe test of cone-beam image quality. FIG. 10A shows a simulated axial scan on a 32×0.75 mm detector array. The z position of 9 mm is 75% of the maximum 12 mm to the edge of the detector rows. The use of variable angular weighting based on the detector aperture function G(Z) enables accurate reconstruction at this large z position. In FIG. 10B, a 360° reconstruction according to the prior art, which is possible only for a z position up to 7.2 mm, is shown for comparison.

The invention has been described with reference to the preferred embodiments. obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An image reconstruction method for reconstructing cone or wedge-beam computed tomography projection data, the method comprising:

weighting projection data based on at least one of its angular orientation and its location within a detector aperture; and reconstructing the weighted projection data to form a volume image representation.

2. The image reconstruction method as set forth in claim 1, further including:

prior to the weighting, re-binning the projection data to associate projection data having the similar angular orientation.

3. The image reconstruction method as set forth in claim 2, wherein the weighting step includes:

distributing re-binned projection data associated with a selected image element which one of (a) has the same angular orientation and (b) is angularly separated by integer multiples of 180° into a selected one or more of a plurality of parallel processing pipelines; and combining the outputs of the selected one or more parallel processing pipelines to produce weighted projection data.

4. The image reconstruction method as set forth in claim 3, wherein the combining includes:

summing the outputs of the selected one or more parallel processing pipelines; and applying a normalization factor computed from the weightings of the selected one or more parallel processing pipelines.

5. The image reconstruction method as set forth in claim 3, wherein the distributing includes distributing re-binned data into a selected one, two, three, or four pipelines.

6. The image reconstruction method as set forth in claim 1, wherein the weighting and the reconstructing cooperate to calculate a volume element value V(x,y,z) corresponding to a selected image element according to:

$$V(x, y, z) = \sum_{n=1}^{N} \left[ \sum_{m=1}^{M} \frac{W_n G_m P_{n,m}}{\sum_{m'=1}^{M} W_n G_{m'}} \right]$$

where m and m' index data sets having corresponding data separated by angular multiples of 180°, n indexes the projection angular orientation, $P_{n,m}$ corresponds to projection data, and $W_n$ and $C_m$ correspond to angular and detector aperture weightings, respectively, applied in the weighting step.

7. The image reconstruction method as set forth in claim 1, further including:

combining weighted projection data from a selected number of projection data sets associated with a selected volume element, the projection data sets being angularly congruent modulo 180°, to produce the weighted projection data.

8. The image reconstruction method as set forth in claim 7, wherein the reconstructing includes:

backprojecting the weighted projection data.

9. The image reconstruction method as set forth in claim 8, wherein the backprojecting includes calculating a volume element value V(x,y,z) corresponding to each selected image element according to:

$$V(x, y, z) = \sum_{n=1}^{N} P_{out}$$

where n indexes the re-binned projection viewing angle, and $P_{out}$ is the weighted projection data.

10. The image reconstruction method as set forth in claim 1, further including:

dividing an image area corresponding to the image representation into a plurality of sub-matrices;

applying the weighting step and the reconstructing step to projection data associated with a selected sub-matrix to form a sub-matrix image representation;

repeating the applying for each sub-matrix to form a plurality of sub-matrix image representations; and combining the sub-matrix image representations to form the image representation.

11. The image reconstruction method as set forth in claim 1, wherein the weighting step includes:

weighting projection data based on its location in a detector aperture using an aperture weighting look-up table.

12. The image reconstruction method as set forth in claim 1, wherein the weighting step includes:

weighting projection data based on its location within a detector aperture, the location within the detector aperture being estimated using a parabolic approximation.

13. The image reconstruction method as set forth in claim 1, wherein the weighting step includes applying a detector aperture weighting that extends beyond the physical aperture edges, and the image reconstruction method further includes:

extrapolating projection data beyond the detector aperture, the extrapolated projection data being weighted according to the portions of the detector aperture weighting that extend beyond the physical aperture edges.

14. The image reconstruction method as set forth in claim 1, wherein the projection data include angular orientations spanning a 180° angular range and an overscan range outside the 180° angular range, the weighting step including:

applying complementary angular weighting to projection data having angular orientations in the overscan range lying above and below the 180° angular range.

15. The image reconstruction method as set forth in claim 1, wherein the weighting step includes:

weighting projection data based on its location in a detector aperture using an aperture weighting function $G(Z+kU)$ that defines a virtual aperture with slanted edges.

16. The image reconstruction method as set forth in claim 1, wherein the weighting step includes:

applying angular weighting for reducing a magnitude of projection data collected outside of a selected angular window.

17. The image reconstruction method as set forth in claim 1, further including:

uniformly interpolating projection data in a Z-direction, the interpolating including at least correcting for an angular variation in a V-direction.

18. The image reconstruction method as set forth in claim 1, further including:

distance-weighting projection data to correct for an angular divergence of a wedge-beam.

19. A computed tomography imaging apparatus for reconstructing cone or wedge beam projection data, the apparatus comprising:

a weighting means for weighting cone or wedge projection data based on at least one of its angular orientation and its location in a detector aperture; and a reconstructing means for reconstructing the weighted projection data to form a volume image representation.

20. The apparatus as set forth in claim 19 further including:

a radiation source that projects the cone or wedge beam of radiation into an examination region; and a two-dimensional detector array defining a detector aperture arranged to receive at least a portion of the projected radiation, the detector array converting the received radiation into the projection data indicative of absorption between the radiation source and the detector array.

21. The apparatus as set forth in claim 20, further including:

a rotating gantry that rotates at least the radiation source about the examination region; and a support element that supports a subject in the examination region, the support element arranged to move the subject in a linear direction, the rotating gantry and the support element cooperating to effectuate a helical orbit of the radiation source about the subject.

22. The apparatus as set forth in claim 19, wherein the weighting means includes:

a plurality of parallel weighting pipelines that process projection data in parallel, each pipeline weighting selected projection data by at least one of an angular weighting and a detector aperture weighting.

23. The apparatus as set forth in claim 22, wherein the weighting means further includes;

selection circuitry for selectively combining two or more parallel weighting pipelines to weight and combine complementary or redundant projection data having angular coordinates differing by zero or by integer multiples of 180°.

24. The apparatus as set forth in claim 23, wherein the selection circuitry includes:

a control word whose contents control operation of the selection circuitry.

25. The apparatus as set forth in claim 23, wherein the selection circuitry effects parallel processing of other projection data by pipelines that are not included in the selective combining.

26. The apparatus as set forth in claim 25, wherein the parallel processing of other projection data by pipelines that are not included in the selective combining includes:

a second selective combining of two or more parallel weighting pipelines to weight and combine other complementary or redundant projection data having angular coordinates differing by zero or by integer multiples of 180°.

27. The apparatus as set forth in claim 22, wherein each pipeline includes:

an angular weighting processor that applies an angular weighting value based on an angular coordinate; and an aperture weighting processor that applies an aperture weighting value based on a detector aperture coordinate.

28. The apparatus as set forth in claim 27, further including:

an aperture weighting lookup table communicating with the aperture weighting processor for supplying the aperture weighting value to the aperture weighting processor.

29. The apparatus as set forth in claim 19, further including:

a distribution processor that selects complementary or redundant portions of the projection data associated with an element of a selected image matrix and communicates coordinates of the element to the weighting means.

30. The apparatus as set forth in claim 29, wherein the distribution processor includes:

a detector coordinate calculator that calculates a detector aperture coordinate using a non-linear relationship between the detector aperture coordinate and an image matrix coordinate.

31. The apparatus as set forth in claim 29, wherein the distribution processor includes:

a detector coordinate calculator that calculates a detector coordinate corresponding to the element of the image matrix; and an interpolator that calculates a complementary portion of the projection data by interpolating projection data having detector coordinates that are proximate to the detector coordinate calculated by the detector coordinate calculator.

32. The apparatus as set forth in claim 19, further including:

a look-up table that selects projection data for spatially uniform interpolation in an axial direction.

* * * * *